United States Patent [19]
Tepfer et al.

[11] Patent Number: 5,648,598
[45] Date of Patent: Jul. 15, 1997

[54] ORNAMENTAL CHARACTER OF SCENTED GERANIUMS BY GENETIC TRANSFORMATION

[75] Inventors: David Alan Tepfer, Paris; Jean-Pierre Damon, Savigneux, both of France; Alessandro Pellegrineschi, Rome, Italy

[73] Assignee: Institut National de la Recherche Agronomique, Versailles, France

[21] Appl. No.: 359,874

[22] Filed: Dec. 20, 1994

[51] Int. Cl.$^6$ .............................. A01H 4/00; A01H 1/06; C12M 15/00; C12M 15/82

[52] U.S. Cl. .................. 800/205; 435/172.3; 47/DIG. 1; Plt./87.12

[58] Field of Search .......................... 435/172.3, 172.1, 435/240.4, 145.5; 800/205; Plt./87.12; 47/58, DIG. 1

[56] References Cited

U.S. PATENT DOCUMENTS

| | | | |
|---|---|---|---|
| 4,945,050 | 7/1990 | Sanford et al. | 435/172.1 |
| 5,036,006 | 7/1991 | Sanford et al. | 435/170.1 |
| 5,100,792 | 3/1992 | Sanford et al. | 435/172.1 |
| 5,179,022 | 1/1993 | Sanford et al. | 435/287 |
| 5,204,253 | 4/1993 | Sanford et al. | 435/172.3 |

OTHER PUBLICATIONS

Tepfer, D., "Transformation of Several Species of Higher Plants by Agrobacterium Rhizogenes: Sexual Transmission of the Transformed Genotype and Phenotype", *Cell* 37:959–967 (1984).

Guthrie, "Scented Leaf", *Houseplant Magazine*, pp. 12–14 (1991).

Jung et al., "Use of Genetic Transformation by the Ri DNA of *Agrobacterium rhizogenes* to Stimulate Biomass and Tropane Alkaloid Production in Atropia Belladonna and Calystegia Sepium Roots Grown In Vitro", *Plant Science*, 50:145–151 (1987).

Lambert et al., "Use of *Agrobacterium rhizogenes* to create trangenic apple trees having an altered organogenic response to hormones",*Theor. Appl. Genet.* 85:109–109 (1992).

Li–Yuan Sun et al., "Changes in flowering and the accumulation of polyamines and hydroxycinnamic acid–polyamine conjugates in tobacco plants transformed by the rol Alocus from the $R_i$ TL–DNA of *Agrobacterium rhizogenes*", *Plant Science* 80:145–156 (1991).

Li–Yuan Sun et al., "Modification of phenotype in Belgian endive (*Cichorium intybus*) through genetic transformation by *Agrobacterium rhizogenes:* conversion from biennial to annual flowering", *Transgenic Research* 1:14–22 (1992).

Tepfer et al., "Improvement of Ornamental Characters and Fragrance Production in Lemon–scented Geranium Through Genetic Transformation by *Agrobacterium rhizogenes*", Bio/Technology 12:64–68 (1994).

Tepfer, "$R_i$ T–DNA from *Agrobacterium rhizogenes*, A Semichemical That Alters Morphological Plasticity", *Plant Molecular Biology*, pp. 565–571 (1987).

Tepfer et al., "Control of Root System Architecture Through Chemical and Genetic Alterations of Polyamine Metabolism", *Biology of Adventitious Root Formation*, pp. 181–189 (1994).

*Primary Examiner*—Gary Benzion
*Attorney, Agent, or Firm*—Tilton, Fallon, Lungmus & Chestnut

[57] ABSTRACT

This invention discloses a method for genetically transforming plants of the genus Pelargonium with the soil bacterium *Agrobacterium rhizogenes*. Transformants exhibit improved ornamental characteristics such as a tighter, more globular shape, unwrinkled leaves which are shorter in length and more deeply lobed, a lack of a trailing growth habit, and an increase in fragrance. Under certain conditions, transformants are more resistant to yellowing. In addition, evidence is becoming available that the transformants are more resistant to yellowing flower earlier than controls.

11 Claims, No Drawings

ORNAMENTAL CHARACTER OF SCENTED GERANIUMS BY GENETIC TRANSFORMATION

FIELD OF THE INVENTION

The field of this invention is genetically transformed plants, and more particularly the transformation of ornamental plants to improve their ornamental characteristics.

BACKGROUND OF THE INVENTION

*Agrobacterium rhizogenes* is a soil bacterium that uses a natural system of genetic transformation to insert $R_i$ T-DNA into the genome of dicotyledonous plants. $R_i$ T-DNA is composed of TL (left) and TR (right) segments. D. Tepfer, "Transformation of Several Species of Higher Plants by Agrobacterium Rhizogenes: Sexual Transmission of the Transformed Genotype and Phenotype", *Cell*, 37:959–967 (1984).

The presence of the $R_i$ T-DNA causes the formation of genetically transformed roots which can give rise to whole plants carrying foreign genes. The transformed roots are genetically stable and easy to manipulate. P. Guerche et al., "Genetic Transformation of Oil Seed Rape (Brassica napas) by the $R_i$ T-DNA of *Agrobacterium rhizogenes* and Analysis of inheritance of the transformed phenotype", *Mol. Gen. Gent.* 206:382–386 (1987), hereby incorporated by reference. The roots are characterized by rapid growth, altered geotropic behavior, and a high degree of branching. Apical dominance is reduced, more laterals form and the general propensity to differentiate root meristems is increased, and morphological plasticity is augmented. D. Tepfer, "$R_i$ T-DNA from *Agrobacterium rhizogenes*, A Semichemical That Alters Morphological Plasticity", *Plant Molecular Biology*; pgs. 565–571 (1987), hereby incorporated by reference.

The genetically transformed roots, in many species, give rise to whole plants carrying the T-DNA genes. Such whole plants exhibit a transformed phenotype which includes increased branching, shortened stature, wrinkled leaves, modified flowering, annualism in biennials, and more branched root systems. C. Lambert and D. Tepfer, "Use of *Agrobacterium rhizogenes* to create trangenic apple trees having an altered organogenic response to hormones", *Theor. Appl. Genet.* 85:105–109 (1992). A good description of the transformed phenotype can be found in D. Tepfer, "$R_i$ T-DNA from *Agrobacterium rhizogenes*, A Semichemical That Alters Morphological Plasticity", *Plant Molecular Biology*; pgs. 565–571 (1987). In addition, in the axenic root cultures of *Calystegia sepium* and *Atropa belladonna*, genetic transformation by $R_i$ T-DNA increases biomass and tropane alkaloid production. See G. Jung and D. Tepfer, "Use of Genetic Transformation by the $R_i$ T-DNA of *Agrobacterium rhizogenes* to Stimulate Biomass and Tropane Alkaloid Production in *Atropia Belladonna* and *Calystegia Sepium* Roots Grown In Vitro", *Plant Science*, 50:145–151 (1987).

It is known that $R_i$ TR-DNA carries genes responsible for auxin and opine synthesis. $R_i$ TL-DNA carries genes that alter development and phenotype. $R_i$ TL-DNA is known to induce the following developmental and phenotypic changes: reduced apical dominance, shortened internodes, root plagiotropism, partial sterility, annualism in biennials and leaf wrinkling. See Li-Yuan Sun et al., "Modification of phenotype in Belgian endive (*Cichorium intybus*) through genetic transformation by *Agrobacterium rhizogenes*: conversion from biennial to annual flowering", *Trangenic Research* 1:14–22 (1992) and Li-Yuan Sun et al., "Changes in flowering and the accumulation of polyamines and hydroxycinnamic acid-polyamine conjugates in tobacco plants transformed by the rol A locus from the $R_i$ TL-DNA of *Agrobacterium rhizogenes*", *Plant Science* 80:145–56 (1991).

$R_i$ TL-DNA has been sequenced and contains 18 stretches of DNA sequences that do not contain any stop condons. (Such areas are referred to as an open reading frame.) The 18 stretches of DNA sequences encode putative proteins of 100 amino acids or more. Through the use of insertional mutagenesis, some of the open reading frames have been recognized as being important in root induction. These are the "rol" (root locus) genes, which are designated A–D. F. White, B. Taylor, G. Huffman, M. Gordon and E. Nester, "Molecular and genetic analysis of the transferred DNA regions of the root inducing plasmid of *Agrobacterium rhizogenes*," *J. Baceriol.*, 164 (1985) 33–44. In experiments conducted with tobacco, it was discovered that the dwarfing of aerial parts can generally be assigned to both rol A and rol C; wrinkled leaves are primarily due to rol A; and reduced apical dominance is due to rol C. D. Tepfer et al., "Control of Root System Architecture Through Chemical and Genetic Alterations of Polyamine Metabolism", *Biology of Adventitious Root Formation*, pgs. 181–189 (1994); see also Li-Yuan Sun et al., "Changes in flowering and the accumulation of polyamines and hydroxycinnamic acid-polyamine conjugates in tobacco plants transformed by the rol A locus from the $R_i$ TL-DNA of *Agrobacterium rhizogenes*", *Plant Science* 80:145–156 (1991). T. Schmülling, J. Schell and A. Spena, "Single genes from *Agrobacterium rhizogenes* influence plant development," *EMBO J.*, 7 (1988) 2621–2629; V. Sinkar, F. Pythoud, F. White, E. Nester and M. Gordon, "rol locus of the Ri plasmid directs developmental abnormalities in transgenic plants," *Genes and Dev.*, 2 (1988) 688–698; V. Sinkar, F. White, I. Furner, M. Abrahamsen, F. Pythoud and M. Gordon, "Reversion of aberrant plants transformed with *Agrobacterium rhizogens* is associated with the transcriptional inactivation of the TL-DNA genes", *Plant Physiol.*, 86 (1988) 47–57.

Ornamental plants such as geraniums and scented geraniums decorate gardens and balconies where they provide a diverse spectrum of fragrance. The scents of the leaves range anywhere from lime and lemon to strawberry, peach, coconut, and rose. The scent originates from oils released by glands on the leaves.

While scented geraniums produce pleasant fragrances, the plants otherwise have rather unpleasant ornamental characteristics, such as an unattractive plant habit. It is therefore the principal object of this invention to provide genetically transformed geraniums having improved ornamental characteristics.

SUMMARY OF INVENTION

Plants of the genus Pelargonium are comprised principally of the species and varieties known as "scented geraniums" but also include the commercially important zonal and ivy geranium species. Scented geraniums extrude pleasing odors but are of little horticultural interest for their flowers. The uses of scented geraniums for home gardens has been limited because of their unattractive appearance. For example, scented geraniums usually have a trailing growth habit. The plants also can appear unattractive due to their long internodes and chaotic, ungainly growth.

The present invention is based on the discovery of a method for genetically modifying plants of the genus Pelargonium to markedly improve their ornamental characters. The genetic transformation is achieved by a procedure which heretofore has been applied almost entirely to non-ornamental plants such as tobacco or carrot. This procedure employs T-DNA of the $R_i$ plasmid *Agrobacterium rhizogenes*. In the past, phenotypes resulting from $R_i$ T-DNA genetic modification have been characterized by leaves which are wrinkled giving a crinkled unattractive appearance.

Leaf wrinkling makes an ornamental plant less attractive. It was therefore of importance to find that the introduction of the $R_i$ T-DNA into geraniums results in a phenotype without a leaf wrinkling characteristic, even though the leaves are shortened in length.

Another unexpected improvement is that transformed scented geraniums provide enhanced fragrance. This is due to increased content in the leaves of the scent-bearing essential oils. Further, under certain growth conditions, the leaves of the transformed plants can be more resistant to yellowing.

The growth characteristics of the geraniums are also improved. The trailing growth habit of the plants is substantially eliminated, and the transformed plants have a more globular shape, which improves their attractiveness.

Other phenotypic traits previously associated with *Agrobacterium rhizogenes* T-DNA insertion are obtained. For example, more adventitious roots and more branch roots are produced. Above ground, the plants have shortened internodes with increased branching.

DETAILED DESCRIPTION OF THE INVENTION

Scented geraniums of the genus Pelargonium release pleasant odors but have unattractive growth habits. Most scented geraniums have long internodes, chaotic, ungainly growth and a trailing growth habit. The present invention provides a method of genetically transforming scented geraniums to improve their ornamental characteristics.

To obtain the genetically transformed scented geranium plants of this invention, the soil bacterium *Agrobacterium rhizogenes* (*A. rhizogenes*) is employed. *Agrobacterium rhizogenes* is known to use a natural system of genetic transformation to insert $R_i$ T-DNA into the genome of dicotyledonous plants. The presence of the $R_i$ T-DNA causes the formation of genetically transformed roots which gives rise to whole plants carrying the T-DNA genes.

Any wild-type strain of *A. rhizogenes* can be used in this invention. For example, wild-type strains designated as A4, LBA9402, 8196, K-47, A4RSII, and 15834 can be used. These strains are in general circulation in the scientific community and are available upon request. For example, strains suitable for use in this invention are available from the American Type Culture Collection and other known depositories as well as from the Institut National de la Recherche Agronomique (INRA) in Versailles, France.

A single strain or a mixture of several bacterial strains can be used in this invention. It is preferred that a mixture of several bacterial strains be used because it improves efficiency and likelihood that at least one strain will be highly infectious on any given plant.

The bacterial strains are grown over night in any suitable medium that fosters growth, such as potato dextrose broth (PDB). The strains are cultured in a rotary shaker at 150 rpm at a temperature between 25°–30° C. After incubation, the turbidity ($As_{590}$) of the cultures is determined using a spectrophotometer. Turbidity refers to how much light is absorbed or reflected as it passes through a solution. Turbidity is often used to refer how "cloudy" a solution is. For bacterial cell suspensions, the more cells per milliliter of water, the more turbid the suspension.

Based on the turbidity of the cultures, an equal number of cells from each strain are mixed together. The cell mixture is used as inoculum for infection. Although a cell mixture containing several wild-type strains may be adventageous, a cell mixture containing only a single strain of *A. rhizogenes* can also be used.

The scented geraniums to be genetically transformed may be any plants of the genus Pelargonium. Plant material, such as cuttings and fragments, and whole live plants can be transformed. Cells from live plants can also be transformed using the biolistic method and apparatus described in U.S. Pat. Nos. 4,945,050, 5,036,006, 5,100,792, 5,179,022, and 5,204,253, hereby incorporated by reference.

The plant material to be transformed can be obtained from live plants grown in a greenhouse or in vitro. If greenhouse grown plants are used, the plant material must be surface sterilized. Many methods of surface sterilization are known in the art and can be used in this invention. For example, surface sterilization can be accomplished in three steps. First, the plant material is rinsed three times in tap water, washed for one minute in a solution of detergent such as 0.5% "SPARKLEEN" (Calgon Vestal Lab Inc., St. Louis, Mo.), and rinsed three times with tap water. Second, the plant material is rinsed for at least 30 seconds in an alcohol, such as 70% ethanol and then soaked for 15 minutes in a combination of bleach, such as 20% "CLOROX", and a detergent, such as 0.5% "SPARKLEEN". Third, the plant material is rinsed several times in sterile distilled water.

If in vitro grown plants are to be used, the plant material is simply harvested; no surface sterilization is required. If whole live plants are to be transformed, greenhouse grown plants can be used; however, no surface sterilization is required.

Inoculation is carried out by contacting sterile plant material or a whole live plant with the cell mixture for several minutes. However, before inoculation with the cell mixture, the plant material or plant must first be wounded to provide a site of entry for the bacteria. The wound is made in addition to the already existing cut surfaces made in obtaining the tissue pieces. The wound can be made anywhere on the plant material or plant, using any laboratory instrument suited for such a purpose. For example, if leaf pieces (1 cm wide strips) or petioles (1.5 cm segments) are to be inoculated, they are dipped in the *A. rhizogenes* cell mixture for at least two minutes. As the plant material is being placed in the cell mixture, it is wounded by gently squeezing between forcep tips. If a whole live plant is used, the cell mixture is placed in contact with the wound on the plant for several minutes. Controls should be included for each plant variety that is transformed. The controls are wounded and exposed to water.

After several minutes, the inoculated plant tissue is removed from contact with the cell mixture, blotted on sterile filter paper, and placed on a medium that fosters rapid growth. Whole plants do not need such treatment, but simply continue to grow in the greenhouse. The preferred medium is an MS based medium containing no growth regulators or hormones. See Murashiage, T. and Skoog, F. 1962, (A Revised Medium for Rapid Growth in Bioassays with Tobacco Tissue Cultures.) *Physiol. Plant.* 15:473–497. The inoculated plant tissue is placed in the dark at a temperature between 20°–25° C. for at least 48 hours to promote infection.

After 48 hours, the inoculated plant tissue is transferred to a fresh medium, an antibiotic is added to the medium to inhibit growth of *A. rhizogenes*. Any antibiotic that inhibits the growth of *A. rhizogenes* can be used, such as cefotaxime, carbenicillin and vancomycin. The amount of antibiotic to be used varies with the antibiotice. However, it is preferred that the medium contain 200 mg/L of cefotaxime. The inoculated plant tissue is transferred every 14 days to fresh medium containing an antibiotic.

Once the Ri T-DNA is inserted into the host genome, cell division occurs at the site of inoculation. If infection is successful, roots begin to appear from the infected plant tissue approximately two weeks after inoculation. Each root arising from a unique wound site is considered to be a transformation event. When the roots are at least one centimeter long, they are cut and placed on a fresh hormone free or growth regulatory free medium containing an antibiotic. Once a week for at least three weeks, the roots are transferred to a fresh medium that contains antibiotic to clean the roots of the *A. rhizogenes*.

Plants can be regenerated from the roots using one of two methods. In the first method, a root tip is transferred to a suitable medium, such as MS based medium, containing a bacterial inhibiting antibiotic such as 200 mg/L cefotaxime. The root tip is incubated at a temperature of about 25° C. with supplementary lighting to provide a 16 hour photoperiod. If a true transformant, the root continues to grow, branching and covering the plate. Shoots appear after several months of growth and are removed and placed onto a rooting medium. After the shoots develop roots, the plantlets are transferred to soil. Shoots that spontaneously regenerate from the same root are considered to have originated from the same transformation event.

In the second method, a segment of the root just behind the root tip is placed onto a callus induction medium for at least two weeks and the resulting callused root segment is then transferred to a regeneration medium. The callus on the regeneration medium is incubated at a temperature of about 25° C. with supplementary lighting to provide a 16 hour photoperiod. Shoots and then plantlets that appear are treated as described above.

As the transgenic plants are obtained, they are grown in a greenhouse. No two transformants are exactly the same due to the well-known phenomenon of "position-effects." Therefore multiple transformants are recovered for each geranium genotype to be improved. Individual plants with the most attractive phenotype are selected and increased for commercial release as a new cultivar.

Scented geraniums transformed with *A. rhizogenes* consistently exhibit an improved phenotype when compared to non-transformed scented geranium plants. Importantly, it was discovered that the leaves of the genetically transformed scented geranium plants are not wrinkled. The lack of wrinkling was unexpected and surprising because wrinkling of leaves in plants transformed with *A. rhizogenes* is well documented as an expected change in phenotype. The gene believed responsible for leaf wrinkling in *A. rhizogenes* transformed plants has been located in one of the open reading frames of *A. rhizogenes* and is referred to as rol (root locus) A. See D. Tepfer et al., "Control of Root System Architecture Through Chemical and Genetic Alterations of Polyamine Metabolism", *Biology of Adventitious Root Formation*, pgs 181–189 (1994). The discovery that the leaves are not wrinkled is an improvement in the ornamental character of the plant because leaf wrinkling would make an ornamental plant less attractive. In addition to the lack of wrinkling, the leaves of the transformed plants are smaller in size, more deeply lobed, and have shorter, more upturned petioles.

Another improvement, in the genetically transformed geraniums was enhanced fragrance. The increase in fragrance is correlated with an increase in the content of the leaf of the scent-bearing essential oils. Pellegrineschi et al., "Improvement of Ornamental Characters and Fragrance Production in Lemon-Scented Geranium Through Genetic Transformation by *Agrobacterium rhizogenes*", *Bio/Technology* 12:64–68 (1994), hereby incorporated by reference. For instance, a three to four fold increase in the proportion of geraniol within the essential oils was discovered in transformed plants. Pellegrineschi et al., "Improvement of Ornamental Characters and Fragrance Production in Lemon-Scented Geranium Through Genetic Transformation by *Agrobacterium rhizogenes*", *Bio/Technology* 12:64–68 (1994). The inventors believe that this large increase in production of essential oils could account for the perception of increased fragrance from the leaves of the transformed plants.

The inventors have also found that genetically transformed geraniums contained increased titers of monoterpenes. The increase in monoterpenes is reputed to repulse mosquitos.

Additionally, there is evidence that leaves of the transformed plants can be resistant to yellowing. The inventors found that control "lemon-rose" scented geranium plants grown in a growth chamber yellowed periodically, and then recovered by initiating new growth. Surprisingly, the genetically transformed scented geranium plants grown under the same conditions at the same time resisted yellowing.

Another improvement in the genetically transformed scented geraniums was in their growth characteristics. Nontransformed, control scented geraniums typically have a trailing habit (especially under low light), which gives the plants a spreading, sprawling habit, making them unattractive. A trailing habit occurs in plants that either produce long shoots that only grow horizontally, or that grow upward but then bend laterally and extend their growth in a horizontal direction. However, in scented geraniums transformed according to the method of this invention, the trailing habit is eliminated. Also, the transformed plants have a tighter, more globular shape which makes them more aesthetically appealing than their nontransformed counterparts. Additionally, evidence is now becoming available that the transformed plants flower earlier than non-transformed plants. This earlier flowering, and more branching (with an extra in florescence for each extra branch) would be valuable in those geraniums grown for their flowers.

Other phenotypic traits previously associated with *A. rhizogenes* T-DNA insertion are obtained. The stature of the transformed scented geraniums is reduced due to a decrease in internode length. Lateral branching and leaf number is also increased. The root systems develop faster, are shorter in length and exhibit increased branching. These changes in the root system should be beneficial and allow for the roots to better adapt and exploit the full volume of soil in pots. Furthermore, the increase in root development could speed up propagation.

By way of example, and not limitation, examples of the present invention will now be given.

EXAMPLE 1

*Pelargonium Graveolens* ("Lemon") Scented Geraniums

*Pelargonium graveolens* scented geraniums are commonly grown as ornamental plants and produce a pleasant odor. However, the plant is unattractive due to long internodes, long petioles, large leaves, and chaotic, ungainly growth, and a trailing habit in low light. *A. rhizogenes* was used to correct the essential ornamental defects in this plant.

Plant Material and Propagation:

The plant materials were cuttings from a pot-grown "lemon" scented cultivar of the scented geranium, *Pelargonium graveolens*. The "lemon" cultivar can be obtained from the Centre National de la Recherche Scientifique, Gil-S-Yaetle, France Bacterial Strains and Culture:

A4RSII (a rifampicin and spectinomycin-resistant derivative of the wild type strain A4, containing pRiA4b); LBA9402 (a rifampicin derivative of wild type 1855, containing pRil855); and 15834 (pRil5834). A4RSII and 15834 were maintained in standard medium and LBA9402 in YMB medium containing $K_2HPO_4$ (0.5 g/l), $MgSO_4$, $7H_2O$ (2.0 g/l), NaCl (0.1 g/l), mannitol (10 g/l) and yeast extract (0.4 g/l). Prior to inoculation bacteria were cultured at 28° C. for 24 hours, then centrifuged, washed in sterile water, centrifuged and resupsended in 3 ml of sterile water. Strains were mixed to give equal numbers of bacteria in a final volume of 20 ml. Pellegrineschi et al., "Improvement of Ornamental Characters and Fragrance Production in Lemon-Scented Geranium Through Genetic Transformation by *Agrobacterium rizogenes*," *Bio/Technology* 12:64–68 (1994).

Plant Transformation and Culture:

Petioles were surface-sterilized in a solution of Bayrochlor (Bayrol S. A.) (1 tablet per 200 ml), containing 1 drop of liquid detergent for 20 minutes, then rinsed three times with sterile distilled water, cut into approximately 1 centimeter segments and incubated in the bacterial suspension for five minutes. They were then placed at 22°±2° C. in the dark for 48 hours on MS based medium solidified with 1% agar. Finally they were transferred to the same medium, but containing 200 mg/l cefotaxime to inhibit bacterial growth. Roots appeared on the cut ends of the petioles after 2–4 weeks. They were excised and cultured on MS medium containing 200 mg/ml cefotaxime. Decontamination was facilitated by directing the root tip into the medium. After several centimeters of growth, root tips were transferred to MS based medium lacking cefotaxime. Plantlets appeared in root cultures after several months of growth, and they were transferred to culture vessels and then to pots. Plants were propagated by cutting and maintained in the greenhouse with supplementary lighting to provide a 16 hour photoperiod. For aeroponic mist culture cuttings were wedged into holes in a styrofoam plate, so that the lower extremity was bathed in a nutrient mist produced by a Defensor mist generator.

Transformants are more petite and have a tighter, more globular shape. Roots appeared faster in the transformants and the root system was shorter and more branched than in the controls. Transformants also flowered earlier than the controls. Control plants grown in a growth chamber yellowed periodically, while the transformed plants, grown under the same conditions at the same time, resisted yellowing. Pellegrineschi et al., "Improvement of Ornamental Characters and Fragrance Production in Lemon-Scented Geranium Through Genetic Transformation by *Agrobacterium rhizogenes*," *Bio/Technology* 12:64–68 (1994).

Transformants exhibited an increase in fragrance. An increase in essential oil production, relative to leaf fresh weight, and changes in the composition of the oil produced in the transformed plants was noted. These changes included a three to four fold increase in the proportion of geraniol in the essential oils, which could at least partially account for the perception of increased fragrance from the leaves from the transformed plants. Both increases and decreases were seen in other components, suggesting that transformation caused changes in chemical differentiation.

Leaf shape was different in the transformants: transformed leaves were smaller and more dentate, although the leaf wrinkling normally seen in other genera was absent. Additionally, more branches and leaves were produced per plant. The increase in the number of leaves contributes to the increase production of essential oil. The petioles were shorter and more upwardly curved compared to the controls. Finally, the transformed phenotype was stable: no revisions to a normal or an attenuated phenotype were detected even after intensive propagation through cutting.

EXAMPLE 2

*Pelargonium Denticultatum* ("Old-Spice") Scented Geraniums

Plant Material and Propagation:

The plant materials were cuttings of a pot-grown "Old-Spice" scented cultivar of the scented geranium, *Pelargonium denticulatum*. The "Old-Spice" cultivar can be obtained from Shady Hill Gardens, Batavia, Ill.

Bacterial Strains and Culture:

Same as in Example 1.

Plant Transformation and Culture:

Same as in Example 1.

Results:

Transformants had shorter internodes and petioles. The leaves were shorter in length and not wrinkled. Transformants had a tight, globular shape, no runners, and no trailing habit. Control plants produced horizontally grown runners which resulted in the plants having a spreading, sprawling habit.

EXAMPLE 3

*Pelargonium X Nervosum* ("Lime") Scented Geraniums

Plant Material and Propagation:

The plant materials were obtained from cuttings of a pot-grown "Lime" scented cultivar of the scented geranium, *Pelargonium X nervosum*. The "Lime" cultivar can be obtained from Shady Hill Gardens, Batavia, Ill.

Bacterial Strains and Culture:

Same as in Example 1, except the bacterial strains used were the wild-type strain LBA9402, A4 and 8196. (8196 is a mannopine-type, wild-strain of *Agrobacterium rhizogens*.)

Plant Transformation and Culture:

Same as in Example 1, except stem pieces were used from a greenhouse grown plant instead of petioles. Also stem pieces were wounded by gently squeezing with the forceps before inoculation.

Results:

Transformants had shorter internodes and petioles. The leaves were shorter in length and were not wrinkled. Transformants had petioles that bent slightly upward. Control plant petioles were straight and spiny looking.

EXAMPLE 4

*Pelargonium Graveolens* ("Old Fashioned Rose") Scented Geraniums

Plant Material and Propagation:

The plant materials were obtained from cuttings of a pot-grown "Old Fashioned Rose" scented cultivar of the scented geranium, *Pelargonium graveolens*. The "Old Fashioned Rose" cultivar can be obtained from Shady Hill Gardens, Batavia, Ill.

Bacterial Strains and Culture:

Same as in Example 1, except the bacterial strains used were the wild-type strains LBA9402, A4, 8196, and K-47.

Plant Transformation and Culture:

Same as in Example 1, except petiole and leaf pieces were used from a greenhouse grown plant instead of petioles alone. Plant pieces were wounded, in addition to the cut surfaces, by gently squeezing the tissue between forceps prior to inoculation. Shoots were produced on transformed roots by putting a segment of root on a callusing medium (containing MS salts and the growth hormones BA and MAA) followed by a regeneration medium (containing MS salts and containing the growth hormone Zeatin).

Results:

Transformants had shorter internodes and petioles. The leaves were shorter in length and not wrinkled. Transformants had a tight, globular shape and no runners. Control plants produced horizontally grown runners which resulted in the plants having a spreading, sprawling habit.

EXAMPLE 5

*Pelargonium Tomentosum* ("Peppermint") Scented Geraniums

Plant Material and Propagation:

The plant materials were obtained from cuttings of a pot-grown "Peppermint" scented cultivar of the scented geranium, *Pelargonium tomentosum*. The "Peppermint" cultivar can be obtained from Shady Hill Gardens, Batavia, Ill.

Bacterial Strains and Culture:

Same as in Example 4.

Plant Transformation and Culture:

Same as in Example 4.

Results:

Transformants had smaller leaves, shorter upward curving petioles, and shorter internodes. The leaves were shorter in length and not wrinkled. Control plants are sprawling with long lateral shoots that spread horizontally with large leaves.

EXAMPLE 6

Pelargonium Adoratissimum("Apple") Scented Geraniums

Plant Material and Propagation:

The plant materials were obtained from cuttings of a pot-grown "Apple" scented cultivar of the scented geranium, *Pelargonium adoratissimum*. The "Apple" cultivar can be obtained from Shady Hill Gardens, Batavia, Ill.

Bacterial Strains and Culture:

Same as in Example 4.

Plant Transformation and Culture:

Same as in Example 4.

Results:

Transformants have shorter internodes and leaves are shorter in length which are not wrinkled. Transformants had a tight, globular shape and no trailing habit. Control plants had a larger looser habit, with trailing.

EXAMPLE 7

Standard Zonal Geranium

Plant Material and Propagation:

The plant materials were obtained from cuttings of a pot-grown selection (#360), a standard zonal geranium, *Pelargonium X hortorum*. Standard Zonal Geranium plants are available from Ball Seed Co., West Chicago, Ill.

Bacterial Strains and Culture:

Same as in Example 4.

Plant Transformation and Culture:

Same as in Example 4.

Results:

Transformants have shorter internodes, shorter petioles, more branching, and a more compact shape to the entire plant. Transformants had more flowers due to the increase in branching.

Additional Pelargonium species that have now been modified by the method of this invention include *P. capitatum, P. endsleigh, P. radula, P. rosa*, and *P. vitifolium*. We have transformed eleven different species of the genus Pelargonium, representing an excellent sampling of the total diversity of the species. In every case, this method has yielded transgenic plants with a more attractive phenotype, following the norms of the ornamental industry. Therefore, this method is clearly useful within the Pelargonium species.

Although the invention has been described primarily in connection with the special and preferred embodiments, it will be understood that it is capable of modification without departing from the scope of the invention. The following claims are intended to cover all variations, uses, or adaption of the invention, following, in general, the principles thereof and including such departures from the present disclosure as come within known or customary practice in the field to which the invention pertains, or as are obvious to persons skilled in the field.

We claim:

1. A method of genetically modifying a plant of the genus Pelargonium to modify at least one ornamental characteristic of said plant, the method comprising the steps of, transforming a live Pelargonium plant or live tissue thereof with the T-DNA of the $R_i$ plasmid of *Agrobacterium rhizogenes*, and propagating the resulting transformant to obtain a plant for ornamental use.

2. The method of claim 1 in which said plants are a species or variety of scented geraniums.

3. The method of claim 1 in which said transforming reduces leaf size without resulting in wrinkling of the leaves.

4. The method of claim 2 in which said transforming intensifies the scents of the propagated plants.

5. A method of genetically modifying a Pelargonium species or variety having a unique scent comprising transforming live plants or live tissues of said species or variety with the T-DNA of the $R_i$ plasmid of *Agrobacterium rhizogenes*, and propagating the resultant transformants to obtain plants characterized by improved ornamental characteristics.

6. The method of claim 5 in which said transforming reduces leaf size without resulting in wrinkling of the leaves.

7. The method of claim 6 in which said transforming intensifies the scent of the propagated plants.

8. The method of claim 5 in which said plants prior to transforming have a trailing growth habit and the transformed plants have a globular growth habit.

9. The transformed plants produced by the method of claims 1, 3, 4, 5, 6, or 7 having a modified ornamental characteristic selected from the group consisting of: smaller leaves, more deeply lobed leaves with shorter upturned petioles, increased fragrance correlated with an increase in scent-bearing essential oils, elimination of the trailing habit with a tighter more globular shape plants of reduced stature with increased lateral branching and leaf number, and reduced leaf yellowing.

10. The transformed plants produced by the method of claim 8 having a modified ornamental characteristic selected from the group consisting of: smaller leaves, more deeply lobed leaves with shorter upturned petioles, increased fragrance correlated with an increase in scent-bearing essential oils, reduced stature with increased lateral branching and leaf number, and reduced leaf yellowing.

11. The transformed plants produced by the method of claims 1, 3, 4, 5, 6, 7 or 8 having the modified ornamental characteristics of compact growth habit and shorter internode length.

* * * * *